(12) United States Patent
Jacobsson et al.

(10) Patent No.: US 7,250,061 B2
(45) Date of Patent: Jul. 31, 2007

(54) METHOD OF ANCHORING A PROSTHESIS STRUCTURE

(75) Inventors: Magnus Jacobsson, Mölndal (SE); Lars Carlsson, Kullavik (SE); Björn Albrektsson, Fjäräs (SE); Stig Wennberg, Gunnilse (SE); Tord Röstlund, Kullavik (SE)

(73) Assignee: Astra Tech AB, Molndal (SE)

( * ) Notice: Subject to any disclaimer, the term of this patent is extended or adjusted under 35 U.S.C. 154(b) by 632 days.

(21) Appl. No.: 10/684,922

(22) Filed: Oct. 14, 2003

(65) Prior Publication Data

US 2004/0083005 A1 Apr. 29, 2004

Related U.S. Application Data (63) Continuation of application No. 09/883,251, filed on Jun. 18, 2001, now abandoned, which is a continuation of application No. PCT/SE99/02464, filed on Dec. 21, 1999.

(51) Int. Cl.
*A61F 2/38* (2006.01)

(52) U.S. Cl. .................. 623/20.32; 623/20.21; 623/908

(58) Field of Classification Search ........... 623/20.3, 623/20.11–20.36, 23.4, 23.44, 23.45; 606/1, 606/79
See application file for complete search history.

(56) References Cited

U.S. PATENT DOCUMENTS

| 4,016,606 | A |  | 4/1977 | Murray et al. |
| 4,470,158 | A |  | 9/1984 | Pappas et al. |
| 4,838,891 | A |  | 6/1989 | Branemark et al. ............ 623/20 |
| 4,911,721 | A |  | 3/1990 | Branemark et al. ............ 623/20 |
| 4,919,671 | A |  | 4/1990 | Karpf ............................ 623/20 |
| 4,963,153 | A |  | 10/1990 | Noesberger et al. ........... 623/20 |
| 5,037,439 | A |  | 8/1991 | Albrektsson et al. .......... 623/20 |
| 5,092,895 | A |  | 3/1992 | Albrektsson et al. .......... 623/20 |
| 5,344,458 | A | * | 9/1994 | Bonutti .................... 623/20.32 |
| 5,782,924 | A |  | 7/1998 | Johnson ....................... 623/20 |
| 6,102,954 | A | * | 8/2000 | Albrektsson et al. ..... 623/20.32 |

FOREIGN PATENT DOCUMENTS

| DE | 4011216 | 5/1991 |
| FR | 2630639 | 11/1989 |
| FR | 2630640 | 11/1989 |
| FR | 2691356 | 11/1993 |
| SU | 719625 | 3/1980 |
| WO | 9322990 | 11/1993 |

* cited by examiner

*Primary Examiner*—Brian E. Pellegrino
*Assistant Examiner*—Suba Ganesan
(74) *Attorney, Agent, or Firm*—White & Case LLP (57) ABSTRACT

The invention provides a prosthesis structure for anchorage to the joint end of an articulatory part of a joint in a human or animal body which comprises an engagement element which presents a flat or a substantially flat engagement surface for engaging with a complementary joint end surface provided at the joint end and an elongate fixture connected to and spaced from the engagement surface for insertion into a complementary bore provided at the joint end at a distance from the joint end surface. The invention further provides that the elongate fixture forms an acute angle with the engagement surface.

18 Claims, 4 Drawing Sheets

METHOD OF ANCHORING A PROSTHESIS STRUCTURE

This application is a continuation of U.S. patent application Ser. No. 09/883,251 now abandoned, filed Jun. 18, 2001, which is a continuation of PCT/SE99/02464, filed Dec. 21, 1999.

TECHNICAL FIELD OF THE INVENTION

The present invention relates to a prosthesis structure for anchorage to a joint end of an articulatory part of a joint in a human or animal body comprising an engagement element which presents a flat or substantially flat engagement surface for engagement with a complementary joint end surface provided at the joint end and an elongate fixture connected to and spaced from the engagement surface for insertion into a complementary bore provided at the joint end at a distance from the joint end surface (a "prosthesis of the type defined").

BACKGROUND ART

Prosthesis structures of the type defined are known for use in human knee-joint replacement surgery from prior patent application publications FR-A-2630639 (Le Beguec) and WO93/22990 (Astra AB) with the prosthesis structures made known therein being for anchorage in the knee-joint end of a human tibia or femur respectively. In the prosthesis structures of FR-A-2630639 and WO93/22990 the longitudinal axis of the fixture is oriented parallel to the engagement surface. WO93/22990, the contents of which are incorporated herein by reference, further discloses orienting the fixture at an angle to the main articulation plane of the knee-joint which extends between the extension or anterior side of the joint and the flexion or posterior side of the joint.

The aim of the present invention is to adapt the relation between the elongate fixture and the engagement surface of a prosthesis of the type defined for improving the anchorability of the prosthesis structure.

DISCLOSURE OF THE INVENTION

According to the invention there is provided a prosthesis of the type defined in which the elongate fixture forms an acute angle with the engagement surface. Consequently, by providing the bore with a longitudinal axis which in a predetermined insertion direction is inclined away from the joint end surface at an acute angle which corresponds closely to that formed between the elongate fixture and the engagement surface, the elongate fixture may be inserted into the bore in the predetermined insertion direction such that the elongate surface successively approaches the joint end surface by leading with the end of the elongate fixture spaced farthest from the engagement surface. Moreover, the bore and the joint end surface may be formed at such a distance from each other compared to the distance between the engagement surface and the elongate fixture that the engagement surface of the prosthesis structure is brought into a first contact with the joint end surface at an intermediary insertion position which is short of a final anchored position. As a result, further movement of the prosthesis structure towards the final anchored position will be counteracted by a wedge compression effect and the prosthesis structure will therefore need to be forcibly displaced from the intermediary insertion position in a direction generally parallel with the joint end surface to arrive at the final anchored position. A press-fit and pretensioning forces are thereby obtained between the bone and prosthesis structure resulting in high rotational and lateral stability for the anchored prosthesis structure. Good anchorage for the prosthesis structure to the joint end may therefore be achieved without the use of other fastening means, such as screws and bolts.

The acute angle between the elongate fixture and the engagement surface is preferably in the range of 1° to 5° with the range of 1° to 3° being particularly preferred.

In an embodiment of the invention such as the one hereinafter to be described the elongate fixture is a first elongate fixture and the prosthesis structure comprises one or more further elongate fixtures connected to and spaced from the engagement surface for insertion into complementary bores provided in the joint end at a distance from the joint end surface, each further fixture being inclined at an acute angle to the engagement surface and extending generally in parallel with the first elongate fixture.

The or each fixture may be connected to the engagement surface by one or more rib elements.

In an embodiment of the invention such as the one hereinafter to be described an insertion end portion of the or each fixture is of a reduced cross section. This may be achieved by bevelling the insertion end portion on a side facing towards the engagement surface in which case the insertion end portion is preferably bevelled to such a degree that the side of the insertion end portion facing towards the engagement surface forms an angle with the corresponding side of the remaining portion of the fixture in the range of 1° to 4° with an angle of approximately 2° being particularly preferred.

In an embodiment of the invention such as the one hereinafter to be described the engagement surface is provided with one or more bone tissue receiving cavities which are adapted to receive bone tissue from the joint end surface on anchorage of the prosthesis structure to the joint end. The bone tissue receiving cavities may comprise one or more longitudinal grooves formed in the engagement surface to extend generally in the direction of the or each fixture.

In an embodiment of the invention such as the one hereinafter to be described the or each elongate fixture extends between opposed sides of the engagement element at an inclined angle to the general direction in which the opposed sides extend.

The or each fixture may present a smooth, continuous peripheral surface. Alternately, the or each fixture may be provided with axially extending splines as described in WO93/22990 supra.

In an embodiment of the invention one or more of the surfaces of the prosthesis structure which contact bone tissue when the prosthesis structure is anchored are subjected to a surface treatment for enhancing osseointegration. As an example, there may be mentioned blasting of the bone contacting surfaces.

For convenience, the engagement element and fixture may be formed in one-piece.

In an embodiment of the invention such as the one hereinafter to be described the prosthesis structure is an anchoring component part of a joint prosthesis assembly for partial or total replacement of the joint end of the articulatory part of the joint. To this end, the engagement element may be a plate-like element having a first major surface forming the engagement surface and a second opposite major surface for supporting a further component part or parts of the joint prosthesis assembly.

In an embodiment of the invention such as the one hereinafter to be described the prosthesis structure is adapted for anchorage to the joint end of one of the articulatory parts of a human or animal knee-joint.

BRIEF DESCRIPTION OF THE DRAWINGS

By way of example, embodiments of the invention will now be described with reference to the accompanying Figures of drawings in which:

FIG. 5b is a view in the direction of arrow A in FIG. 5a.

FIG. 5c is a cut-away perspective view in the general direction of arrow A in FIG. 5a.

FIG. 6b is a view in the direction of arrow B in FIG. 6a.

FIG. 6c is a partly cut-away perspective view in the general direction of arrow B in FIG. 6a.

DETAILED DESCRIPTION OF EXEMPLARY EMBODIMENTS

In the Figures of drawings like numbers are used to indicate like parts in the two embodiments.

In FIGS. 1-4 there is shown a bi-condylar knee-joint prosthesis assembly 2 for the tibial side of a knee-joint comprising a prosthesis structure or anchoring component 1 for anchorage to the knee-joint end of a tibia in accordance with the invention.

The prosthesis structure 1 is a one-piece component made from titanium and comprises a plate-like engagement element 3 of non-symmetrical form due to the non-symmetrical nature of the condyles at the knee-joint end of the tibia. The engagement element 3 has a flat-upper surface 3a and a flat lower engagement surface 3b for engagement with a complementary bone tissue surface formed at the knee-joint end of the tibia by resection of the condyles, as will be described in more detail hereinafter.

The prosthesis structure 1 further comprises first and second elongate, parallel rod-shaped fixtures 4, 5 for sliding insertion in an anteroposterior direction into complementary bores drilled between the anterior and posterior sides of the knee-joint end of the tibia at a distance beneath the bone tissue surface formed by resection of the condyles, as will also be described in more detail hereinafter. The first and second fixtures 4, 5 have a smooth, continuous peripheral surface and are connected to the engagement surface 3b of the plate-like engagement element 3 at a spaced distance therefrom by first and second ribs 6, 7.

Figure 4:
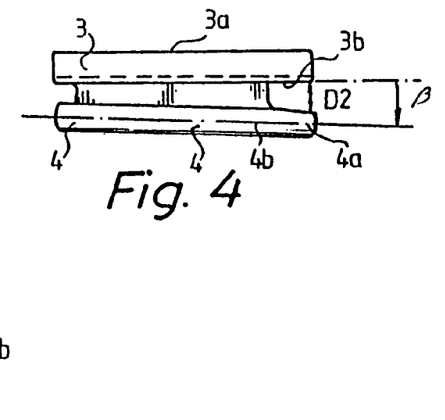
FIG. 4 is a side elevation view of the prosthesis structure of the knee-joint prosthesis assembly in FIG. 1.

Moreover, as illustrated in FIG. 4, each of the first and second rod-shaped fixtures 4, 5 forms an acute angle β with the engagement surface 3b meaning that each fixture has one end (the "leading end") spaced farther from the engagement surface than the other end (the "trailing end"). The acute angle β formed between the first and second fixtures 4, 5 and the engagement surface 3b is in the range of 1° to 5°, preferably approximately 2°.

Figure 2:
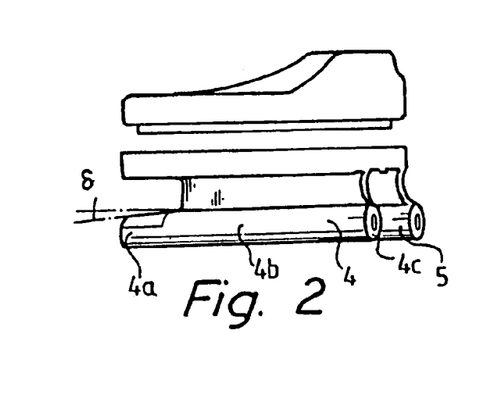
FIG. 2 is a perspective side view of the knee-joint prosthesis assembly in FIG. 1.

As shown in FIG. 2, the leading end of the first fixture 4 is presented by a leading end portion 4a which is of reduced cross-section due to it being bevelled on the upper side facing towards the engagement surface 3b. The bevelled upper side of the leading end portion 4a forms an angle δ with a corresponding upper side of a mid portion 4b of the first fixture and a trailing end portion 4c of the first fixture 4 which presents the trailing end thereof. The bevelled upper side of the leading end portion 4a forms an angle δ with the corresponding upper sides of the mid and trailing end portions 4b, 4c of the first fixture in the range of 1° to 4°, preferably 2°. Although not shown, the second fixture 5 has a correspondingly bevelled leading end portion.

Figure 1:
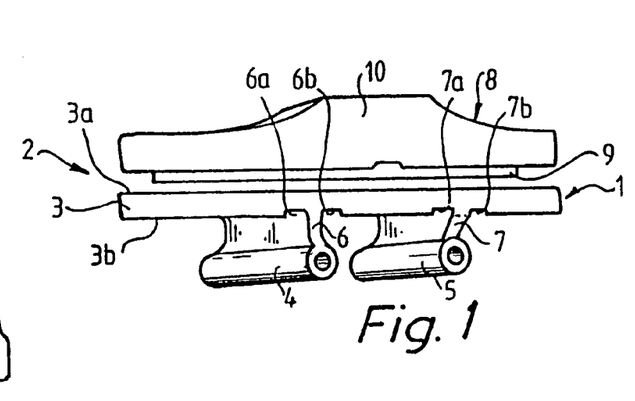
FIG. 1 is a perspective view of a knee-joint prosthesis assembly including a prosthesis structure according to a first embodiment of the invention comprising a plate-like engagement element from which two rod-shaped fixtures having a bevelled end depend.

Referring to FIGS. 1 and 2, the trailing ends of the first and second fixtures 4, 5 are provided with sockets for receiving surgical instruments, e.g. an insertion tool for sliding the first and second fixtures 4, 5 into the complementary bores 12, 13 with the bevelled leading end portions thereof leading.

Figure 3:
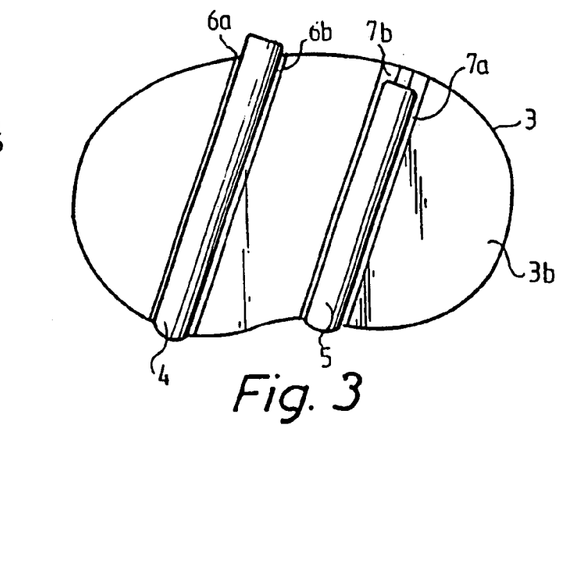
FIG. 3 is a bottom plan view of the prosthesis structure of the knee-joint prosthesis assembly in FIG. 1.

As shown most clearly in FIG. 3, the lower engagement surface 3b is provided with bone tissue receiving cavities 6a, 6b, 7a, 7b in the form of longitudinal grooves extending generally in the direction of the first and second fixtures 4, 5 on either side of the rib elements 6, 7. The bone tissue receiving cavities 6a, 6b, 7a, 7b may instead be stepped or angled up from the engagement surface 3b and their function will be described hereinafter.

As shown in FIGS. 1 and 2, the knee-joint prosthesis assembly 2 also includes an articulating element 8 located on the upper surface 3a of the plate-like engagement element 3 for supporting a femur condyle of the knee-joint or a complementary articulating element of a knee-joint prosthesis assembly anchored to the femur side of the knee-joint. The articulating element 8 comprises a bearing plate 9 mounted on the engagement surface 3b and a sliding element 10 mounted on the bearing plate 9. The upper surface 3a of the plate-like element 3 and the lower surface of the bearing plate 9 are adapted such that the bearing plate 9 is either retained immobile on the upper surface 3a or allowed a specific but restricted movement across the upper surface 3a. The bearing plate 9 may be made of a chromium/cobalt alloy, a chromium/cobalt/molybdenum alloy or a ceramics material. The sliding element 10 may be made of a durable plastics material such as ultra high molecular weight polyethylene.

Prior to performing the procedure for implanting the knee-joint prosthesis assembly 2, the patient will have undergone a pre-operational X-ray study and planning phase during which the measurements and parameters needed to allow a correct selection of dimensions for the elements of the prosthesis assembly 2 will have been determined. The implantation operation may then be carried out using generally the same procedure disclosed in WO 93/22990 supra. Implantation may be carried out in a one-stage operation.

Figure 5A:
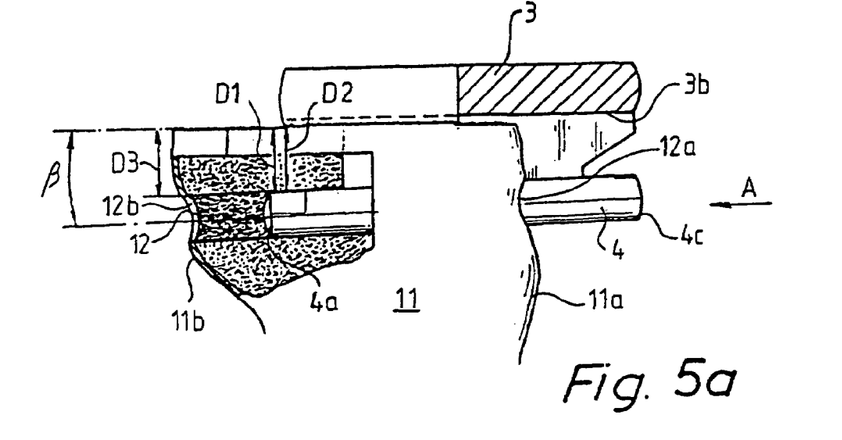
FIG. 5a is a side view, partly in cross-section, of the prosthesis structure of the knee-joint prosthesis assembly in FIG. 1 positioned in an intermediary insertion position during the fitting thereof in the prepared bone tissue at the condylar end of a tibia.
Figure 5B:
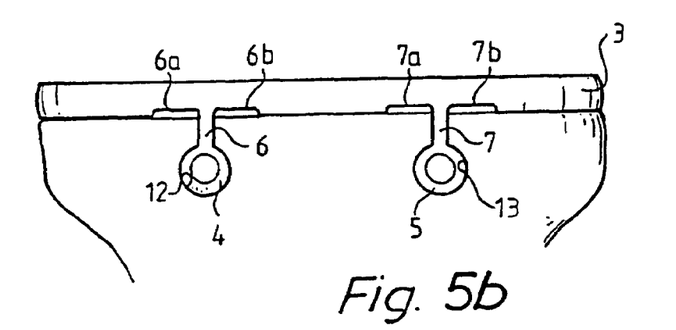
Figure 5C:
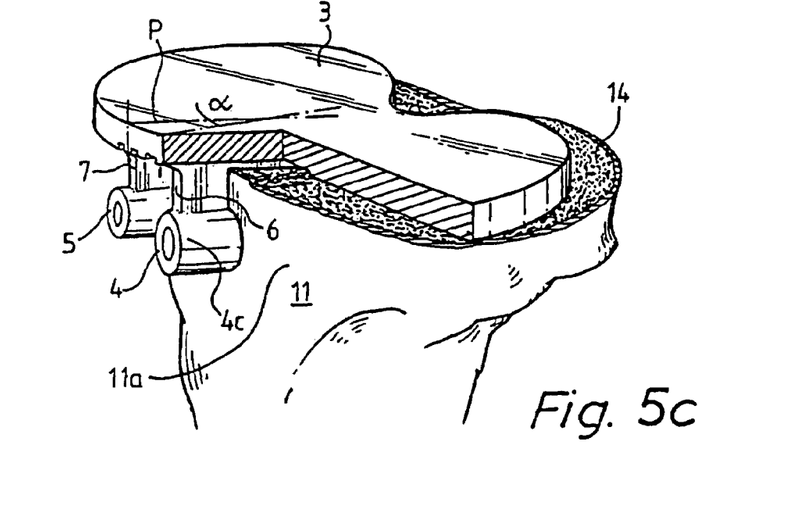

As shown in FIGS. 5a-5c, first and second bores 12, 13 are drilled through the knee-joint end of the tibia 11 in the anteroposterior direction. The anterior or front end of the first bore 12 is denoted 12a and the posterior or rear end denoted 12b. The diameter of the first and second bores 12, 13 is such that they closely correspond to the diameters of the first and second fixtures 4, 5. The first and second bores 12, 13 are located in relatively healthy bone by virtue of the first and second bores 12, 13 being offset from the extremity of the knee-joint end of the tibia 11 thereby serving to further promote osseointegration of the first and second fixtures 4, 5 when inserted into the first and second bores 12, 13. The osseointegratability of the first and second fixtures 4, 5 may be further enhanced by roughening or texturing the surfaces thereof, for example by grit blasting. The same surface enlargement treatment could also be applied to the engagement surface 3b to promote the osseointegratability of that surface.

After the drilling operation, the condyles of the tibia 11 are resected to give a bone surface 14 which is of complementary shape to the engagement surface 3b, as shown in FIG. 5c. The resected bone surface 14 will typically be inclined to horizontal in the anteroposterior direction when the patient stands upright to support the functional motions of the knee-joint. The angle of inclination of the resected bone surface 14 to horizontal is in the range of 2° and 9°, preferably approximately 6°. Referring to FIG. 5b, first and second slots 15 and 16 are provided between the resected bone surface 14 and the first and second bores 12, 13 respectively for passage of the first and second rib elements 6 and 7 on insertion of the first and second fixtures 4, 5 into the first and second bores 12, 13.

As shown in FIG. 5a, the first and second bores 12, 13 each form an angle with the resected bone surface 14 which corresponds to the angle β between each of the first and second rod-shaped fixtures 4, 5 and the flat engagement surface 3b, the angulation of the first and second bores 12, 13 being such that the posterior ends of the first and second bores 12, 13 are spaced farther from the resected bone surface 14 than the anterior ends. For this reason, the engagement surface 3b of the prosthesis structure 1 will successively approach the resected bone surface 14 as the leading ends of the first and second fixtures 4, 5 are inserted into the first and second bores 12, 13 in an anteroposterior direction.

It will be noted from FIG. 3 that the first and second fixtures 4, 5 extend between opposing sides of the plate-like engagement element 3 at an inclined angle to the general direction in which the opposed sides-extend. As can be seen from FIG. 5c, the first and second bores 12, 13 are correspondingly angled between the anterior and posterior sides 11a, 11b of the tibia resulting in the first and second fixtures 4, 5 forming an angle α with a main articulation plane P of the knee-joint which extends essentially vertically between the anterior and posterior sides 11a, 11b of the tibia 11 when the first and second fixtures 12, 13 are inserted into the first and second bores 12, 13. The angle a with the main articulation plane P of the knee-joint is in the range of 10° to 45°, preferably approximately 20°

In view of the first and second fixtures 4, 5 being inserted into the tibia 11 at an angle a to the main articulation plane P, the first and second fixtures 4, 5 are given different lengths so that (i) the first and second fixtures 4, 5 enter the anterior ends of the first and second bores 12, 13 at substantially the same time, (ii) emerge from the posterior ends of the first and second bores 12, 13 at substantially the same time, and (iii) preferably do not project from the anterior ends of the first and second bores 12, 13 in a final anchored position of the prosthesis structure 1.

FIG. 4 shows that the leading end portion 4a of the first fixture 4 is spaced from the engagement surface 3b of the plate-like engagement element 3 by a predetermined distance D2. This is further the case for the second fixture 5 (not shown). Referring now to FIG. 5a, it can be seen that the first and second bores 12, 13 are so positioned relative to the resected bone surface 14 that an intermediary position between the anterior and posterior ends of the first and second bores 12, 13 is spaced from the resected bone surface 14 by a predetermined distance D1 which is equal to the distance D2 between the engagement surface 3b and the leading end portions of the first and second rod-shaped fixtures 4, 5. The result of this dimensioning is that the engagement surface 3b of the engagement element 3 of the prosthesis structure 1 is brought into a first contact with the resected bone surface 14 at an intermediate insertion position short of the final anchored position.

Figure 6A:
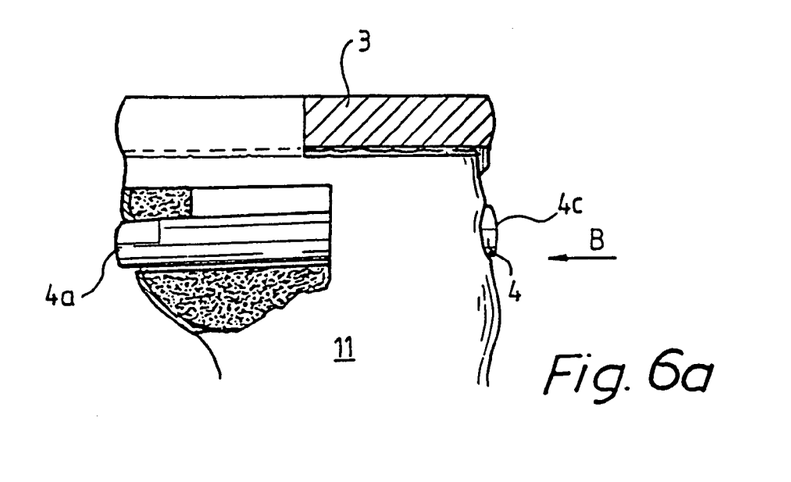
FIG. 6a is a side view, partly in cross-section, of the prosthesis structure of the knee-joint prosthesis assembly in FIG. 1 in a fully inserted, anchored position at the condylar end of the tibia.
Figure 6B:
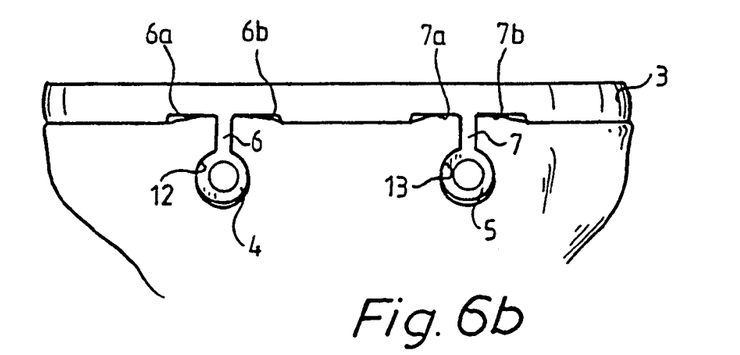
Figure 6C:
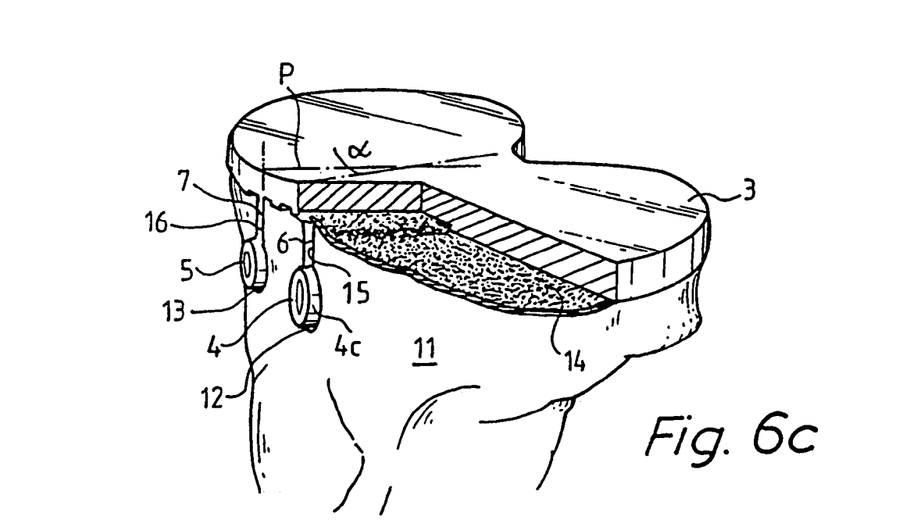

The intermediate insertion position of the prosthesis structure 1 is shown in FIGS. 5a-c from which it will be appreciated that movement of the prosthesis structure 1 from the intermediate insertion position to the final anchored position shown in FIGS. 6a-c will be counteracted by a wedge compression effect because the resected bone surface 14 is spaced from the posterior ends of the first and second bores 12, 13 by a predetermined distance D3 which is greater than the predetermined distance D2 due to the first and second bores 12, 13 being inclined at an angle to the resected bone surface 14. The difference between the predetermined distances D3 and D2 will typically be within the range of 0.1 to 0.9 mm with a difference of approximately 0.35 mm being preferred. As an example, the predetermined distance D3 may be approximately 10 mm. It will be gathered from the foregoing that the prosthesis structure 1 has to be forcibly displaced from the intermediate insertion position in a direction essentially parallel with the resected bone surface 14 to arrive at the final anchored position illustrated in FIGS. 6a-c to overcome the wedge compression effect.

As illustrated in FIGS. 6a-c, the wedge compression effect results in bone tissue from the resected bone surface 14 being forced into the bone tissue receiving cavities 6a, 6b, 7a, 7b in the engagement surface 3b of the engagement element 3 as the prosthesis structure 1 is forcibly displaced from the intermediate insertion position to the final anchored position. Moreover, the wedge compression effect results in the resected bone surface 14 being compressed against the engagement surface 3b. This creates pretensioning forces between the engagement surface 3b and the resected bone surface 14 and also between the upper sides of the first and second rod-shaped fixtures 4, 5 and the bone tissue in the first and second bores 12, 13. For this reason, the prosthesis structure 1 may be anchored in the tibia 11 by a press-fit and pretensioning forces alone, that is to say, without the need for using any other fastening means such as screws and bolts. The prosthesis structure 1 will also have a high rotational and lateral stability in the final anchored position due to the wedge compression effect.

Figure 7:
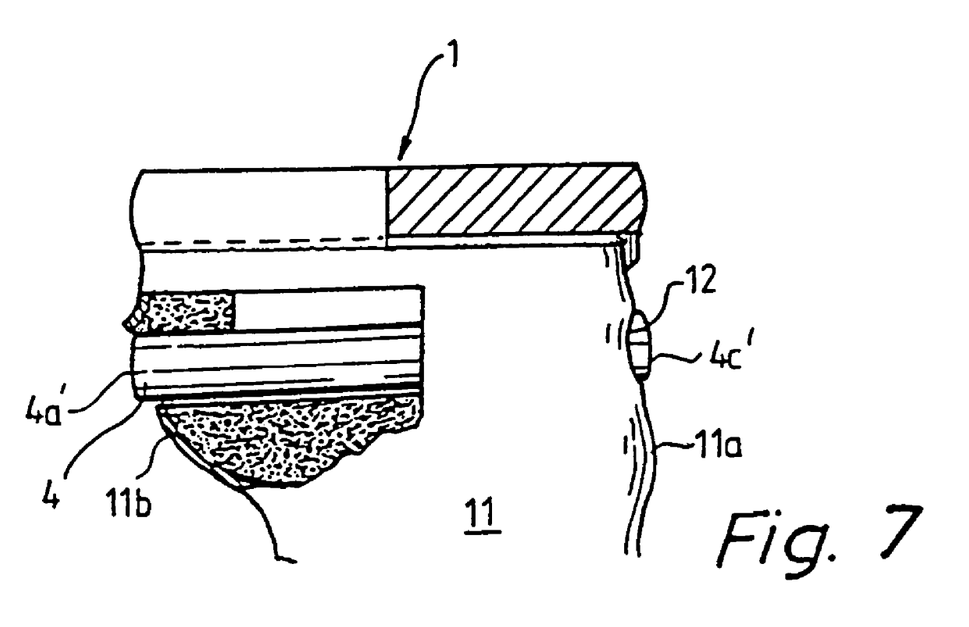
FIG. 7 is a side view, partly in cross-section, of a prosthesis structure for a knee-joint prosthesis assembly according to a second embodiment of the invention which corresponds to the first embodiment in FIGS. 1-6 other than that the ends of the rod-shaped fixtures are not bevelled.

The reason for bevelling the leading end portions of the first and second fixtures 4, 5 is illustrated by the embodiment shown in FIG. 7 in which the first (and second fixture) 4 has an leading end portion 4a' which is not bevelled. During displacement of the prosthesis structure 1 from the intermediate insertion position to the final anchored position the unbevelled leading end portion 4a' digs itself into the bone and creates a pressure in front of it which may result in a splitting of the posterior cortical bone and a loss of the pretensioning forces in a posterior part of the anchored prosthesis structure 1.

Several modifications of the embodiments described above with reference to the Figures of drawings are conceivable within the ambit of the invention. For example, instead of having a smooth continuous surface the fixtures could be splined as shown in WO 93/22990 supra or slotted to increase the interference thereof with bone tissue. The engagement surface of the engagement element may likewise be splined as shown in WO 93/22990 for increasing stability. In addition, more than two fixtures could be used if desired and in a basic form of the invention only a single fixture is used. The bone tissue receiving cavities provided in the engagement surface could also be omitted without detracting from the invention. Moreover, it will be appreciated by those versed in the art that prosthesis structures in accordance with the invention may be used at the femur side of a knee-joint or at a joint member of another human or animal joint.

The invention claimed is:

1. A method of anchoring a prosthesis structure to a joint end of an articulatory part of a joint in a human or animal body, said prosthesis structure comprising an engagement element which presents a flat or substantially flat engagement surface and an elongate fixture having a major axis and being connected to and spaced from the engagement surface, the method comprising the steps of:
   forming a flat or substantially flat joint end bone surface at said joint end;
   forming a bore through said joint end, wherein the bore has a longitudinal axis which inclines away from the joint end bone surface at an acute angle, and wherein the bore is provided at a distance from said joint end bone surface;
   forming a slot between the joint end bone surface and the bore; and
   inserting said elongate fixture along said major axis into the bore so that said engagement surface is brought into a first contact with said joint end bone surface at an intermediate insertion position; and
   further displacing the elongate fixture along the longitudinal axis of the bore to bring the engagement surface from the intermediate insertion position to a final anchored position.

2. The method as claimed in claim 1, wherein the prosthesis structure further comprises a rib element connecting the elongate fixture and the engagement element and the step of inserting said elongate fixture further comprises inserting said rib element into said slot.

3. The method as claimed in claim 1, wherein said bore is a first bore and the method further comprises forming, at a distance from said joint end bone surface, at least one additional bore extending generally in parallel with said first bore for receiving a corresponding number of elongate fixtures.

4. The method as claimed in claim 3, wherein said slot is a first slot and the method further comprises forming an additional slot between each additional bore and the joint end bone surface.

5. The method as claimed in claim 1, wherein the bore is formed relative to the joint end bone surface such that the bore is inclined at an inclination angle relative to a main articulation plane of said joint.

6. The method as claimed in claim 5, wherein the inclination angle is within a range of 10° to 45°.

7. The method as claimed in claim 6, wherein the inclination angle is approximately 20°.

8. A method of anchoring a prosthesis structure to a joint end of an articulatory part of a joint in a human or animal body, said prosthesis structure comprising an engagement element which presents a flat or substantially flat engagement surface and an elongate fixture having a major axis and being connected to and spaced from the engagement surface, the method comprising:
   forming a flat or substantially flat joint end bone surface at said joint end;
   forming a bore through said joint end at a distance from said joint end bone surface;
   bringing the engagement surface of the prosthesis structure into a first contact with the joint end bone surface at an intermediate insertion position of the prosthesis structure by inserting the elongate fixture along said major axis into said bore and in such manner that said major axis inclines away from the joint end bone surface at an acute angle; and thereafter
   further inserting the elongate fixture, along said major axis and at said acute angle, from said intermediate position of the prosthesis structure to a final anchored position of the prosthesis structure, wherein said further inserting of the elongate fixture compresses the complementary joint end bone surface against the engagement surface.

9. The method as claimed in claim 8, wherein the step of further inserting the elongate fixture from said intermediate insertion position to said final anchored position comprises displacing the engagement surface in a direction generally parallel with the joint end bone surface.

10. The method as claimed in claim 8, wherein the bore has a longitudinal axis which inclines away from the joint end bone surface at an acute angle, and wherein said elongate fixture is inserted along said major axis into the bore so as to bring said engagement surface into engagement with said joint end bone surface.

11. The method as claimed in claim 1 or 8, wherein said acute angle is greater than or equal to 1°.

12. The method as claimed in claim 1 or 8, wherein said acute angle is less than or equal to 5°.

13. The method as claimed in claim 1 or 8, wherein said acute angle is within a range of 1° to 3°.

14. The method as claimed in claim 8, wherein said bore is a first bore and the method further comprises:
   forming, at a distance from said joint end bone surface, at least one additional bore extending generally in parallel with said first bore for receiving a corresponding number of additional elongate fixtures; and
   forming a slot between each bore and the joint end bone surface.

15. The method as claimed in claim 8, wherein the bore is formed relative to the joint end bone surface such that the bore is inclined at an inclination angle relative to a main articulation plane of said joint.

16. The method as claimed in claim 15, wherein the inclination angle is within a range of 10° to 45°.

17. The method as claimed in claim 16, wherein the inclination angle is approximately 20°.

18. A method of anchoring a prosthesis structure to a joint end of an articulatory part of a joint in a human or animal body, said prosthesis structure comprising an engagement element which presents a flat or substantially flat engagement surface and an elongate fixture having a major axis and being connected to and spaced from the engagement surface, the method comprising:

forming a flat or substantially flat joint end bone surface at said joint end;

forming a bore through said joint end, the bore having a longitudinal axis, wherein the bore is provided at a distance from said joint end bone surface and wherein said longitudinal axis inclines away from the joint end bone surface at an acute angle; and anchoring the prosthesis to the joint end by the steps comprising:
- inserting said elongate fixture along said major axis into the bore so that said engagement surface approaches said joint end bone surface at an acute angle and is brought into engagement with said joint end bone surface at an intermediate insertion position of the prosthesis structure, and thereafter
- further displacing the elongate fixture, along the bore, from said intermediate insertion position to a final anchored position of the prosthesis structure, wherein the step of further displacing the elongate fixture compresses the complementary joint end bone surface against the engagement surface.

* * * * *

UNITED STATES PATENT AND TRADEMARK OFFICE
CERTIFICATE OF CORRECTION

PATENT NO.         : 7,250,061 B2
APPLICATION NO.    : 10/684922
DATED              : July 31, 2007
INVENTOR(S)        : Jacobsson et al.

Page 1 of 1

It is certified that error appears in the above-identified patent and that said Letters Patent is hereby corrected as shown below:

Title page, ITEM (75) INVENTORS:
For inventor Albrektsson's city of residence, delete "Fjäräs (SE)" and substitute therefor --Åsa (SE)--.

Title page, ITEM (73) ASSIGNEE:
Assignee city should read --MoIndal (SE)--.

Signed and Sealed this

Sixth Day of November, 2007

JON W. DUDAS
*Director of the United States Patent and Trademark Office*